(12) United States Patent
Derzhi

(10) Patent No.: US 8,855,264 B2
(45) Date of Patent: Oct. 7, 2014

(54) METHOD FOR ESTIMATING EFFECTIVE ATOMIC NUMBER AND BULK DENSITY OF ROCK SAMPLES USING DUAL ENERGY X-RAY COMPUTED TOMOGRAPHIC IMAGING

(75) Inventor: Naum Derzhi, Houston, TX (US)

(73) Assignee: Ingrain, Inc., Houston, TX (US)

( * ) Notice: Subject to any disclaimer, the term of this patent is extended or adjusted under 35 U.S.C. 154(b) by 364 days.

(21) Appl. No.: 13/527,660

(22) Filed: Jun. 20, 2012

(65) Prior Publication Data
US 2013/0028371 A1    Jan. 31, 2013

Related U.S. Application Data

(60) Provisional application No. 61/511,600, filed on Jul. 26, 2011.

(51) Int. Cl.
    *G01B 15/02*     (2006.01)
    *G01N 23/087*     (2006.01)
    *G01N 9/24*     (2006.01)

(52) U.S. Cl.
    CPC ............ *G01N 23/087* (2013.01); *G01N 9/24* (2013.01)
    USPC .................................. 378/54; 378/56; 378/5

(58) Field of Classification Search
    CPC ........ A61B 6/032; A61B 6/482; G01N 23/00; G01N 23/02; G01N 23/046; G01N 23/06; G01N 23/083; G01N 9/24; G01B 15/02; G01B 15/025
    USPC ........................ 378/4, 5, 54, 55, 56
    See application file for complete search history.

(56) References Cited

U.S. PATENT DOCUMENTS

| | | |
|---|---|---|
| 4,029,963 A | 6/1977 | Alvarez et al. |
| 4,540,882 A | 9/1985 | Vinegar et al. |
| 4,542,648 A | 9/1985 | Vinegar et al. |
| 4,571,491 A | 2/1986 | Vinegar et al. |
| 4,613,754 A | 9/1986 | Vinegar et al. |
| 5,063,509 A | 11/1991 | Coles et al. |
| 5,164,590 A | 11/1992 | Coles et al. |

OTHER PUBLICATIONS

International Preliminary Report on Patentability issued in corresponding International Patent Application No. PCT/US2012/043213 dated Oct. 4, 2013 (21 pages).
Wellington, S.L., et al., "X-Ray Computerized Tomography," Journal of Petroleum Technology, 1987.
Siddiqui, S., et al., "Dual-Energy CT-Scanning Applications in Rock Characterization," Society of Petroleum Engineers, 2004, SPE 90520.
Boyes, J., "The Effect of Atomic Number and Mass Density on the Attenuation of X-rays," Queen's Health Sciences Journal, 2003.
Iovea, M., et al., "Dual-energy X-ray computer axial tomography and digital radiography investigation of cores and other objects of geological interest," Engineering Geology, vol. 103, No. 3-4, pp. 119-126, Feb. 2009.

(Continued)

*Primary Examiner* — Jurie Yun
(74) *Attorney, Agent, or Firm* — Kilyk & Bowersox, P.L.L.C.

(57) ABSTRACT

A method for estimating effective atomic number and bulk density of objects, such as rock samples or well cores, using X-ray computed tomographic imaging techniques is provided. The method effectively compensates for errors in the interpretation of CT scan data and produces bulk densities which have lower residual error compared to actual bulk densities and produces bulk density—effective atomic number trends which are consistent with physical observations.

50 Claims, 8 Drawing Sheets

(56) References Cited

OTHER PUBLICATIONS

Phillips, D. H., et al., "Measuring physical density with X-ray computed tomography", NDT&E International, vol. 30, No. 6, pp. 339-350, Dec. 1, 1997.

International Search Report and Written Opinion issued in corresponding International Patent Application No. PCT/US2012/043213, dated Oct. 31, 2012 (13 pages).

Ayyalasomayajula, K. K., et al., "Analysis of Calibration Materials Materials to Improve Dual-energy CT Scanning for Petrophysical Applications," Society of Petroleum Engineers, 2011, SPE 146522 (pp. 1-11).

Hubbell, J. H., "Photon Cross Sections, Attenuation Coefficients, and Energy Absorption Coefficients From 10 keV to 100 GeV." National Bureau of Standards, vol. 29, Aug. 1969 (90 pages).

Kinahan, P., et al. "Dual Energy CT Attenuation Correction Methods for Quantitative Assessment of Response to Cancer Therapy with PET/CT Imaging." Technology in Cancer Research and Treatment, vol. 5, No. 4., pp. 319-327. Adenine Press, Aug. 2006.

Kumar, T., et al. "Effective Atomic Number Studies in Clay Minerals for Total Photon Interaction in the Energy Region 10keV-10MeV." Radiat. Phys. Chem., vol. 48, No. 6, pp. 707-710. Elsevier Science Ltd., 1996.

Miyajima, S. "The Variations of Mean Mass Energy Absorption Coefficient Ratios in Water Phantoms During X-ray CT Scanning." Proceedings of the Tenth EGS4 Users' Meeting in Japan, KEK Proceedings, 2002-18, pp. 74-83.

METHOD FOR ESTIMATING EFFECTIVE ATOMIC NUMBER AND BULK DENSITY OF ROCK SAMPLES USING DUAL ENERGY X-RAY COMPUTED TOMOGRAPHIC IMAGING

This application claims the benefit under 35 U.S.C. §119 (e) of prior U.S. Provisional Patent Application No. 61/511,600, filed Jul. 26, 2011, which is incorporated in its entirety by reference herein.

BACKGROUND OF THE INVENTION

This invention relates to the field of digital rock physics and specifically to methods to estimate effective atomic number and/or bulk density of rock samples.

Density and effective atomic number measurements of well cores are valuable to reservoir engineers. Bulk densities give an indication of porosity and effective atomic number provides an indication of mineralogy.

There are a number of ways that one can estimate density and effective atomic number including:

1. Physical samples can be withdrawn from the well and density can be measured by weighing the sample, calculating its volume and simply dividing weight by volume.
2. Well logging tools can be used to estimate density and effective atomic number. Gamma-gamma ray techniques are used to estimate density and effective atomic number from the absorption of gamma ray radiation as it passes through the rock in the well bore.
3. X-ray CT scanners can be used to estimate density and effective atomic number by measuring the attenuation of X-rays at two different energy levels and then using the measurements to calculate the density and effective atomic number.

In the 1970's, X-ray computed tomography scanners (CT scanners) began to be used in medical imaging. In the 1980's, these scanners were applied to rock samples extracted from well bores (cores). CT scanners have the advantage of higher resolution than gamma ray logs and they are not affected by environmental conditions as downhole gamma-gamma ray logs are. In addition, CT scanners produce a 3-D distribution of rock properties in the sample, while the logs provide only a 1-D distribution.

Wellington and Vinegar (Wellington, S. L. and Vinegar, H. J., "X-Ray Computerized Tomography," JOURNAL OF PETROLEUM TECHNOLOGY, 1987) reviewed the use of CT scanners in geophysics. The attenuation of X-rays depends upon both electron density (bulk density) and effective atomic number.

$$\mu = \rho\left(a + \frac{bZ^{3.8}}{E^{3.2}}\right) \quad (1)$$

where
$\mu$ is the linear X-ray attenuation coefficient
$\rho$ is the bulk density
Z is the effective atomic number
E is the photoelectric absorption
a and b are constants.

The medical CT scanners provide 3-D volumes of CT values, which are in linear relationship with the attenuation coefficient, $\mu$. The first term in equation (1) is significant at high X-ray energy levels (above 100 kv) while the second term is significant at low X-ray energy levels (below 100 kv).

A dual energy scan can therefore be used to make estimates of both bulk density and effective atomic number. Considering a dual energy scan, equation (1) leads to the following equations:

$$\rho = A*CT_{high} + B*CT_{low} + C \quad (2)$$

$$\rho Z_{eff}^{a} = D*CT_{high} + E*CT_{low} + F \quad (3)$$

where
$\rho$ is the object's density,
$Z_{eff}$ is its effective atomic number,
A, B, C, D, E, F are coefficients,
$CT_{high}$ and $CT_{low}$ are X-ray CT values of the object obtained at high and low energies of X-ray quanta,
$\alpha$ is approximately 3.8.

As indicated, for example, by Siddiqui, A. and Khamees, A. A., "Dual-Energy CT-Scanning Applications in Rock Characterization," SOCIETY OF PETROLEUM ENGINEERS, 2004, SPE 90520, estimating effective atomic number and bulk density distributions in core samples from dual energy X-ray CT involves:

a) Acquiring X-ray CT image of the target object along with at least three objects (calibration objects) with known density and known effective atomic number. In the case of cores, the core axis is aligned with the Z axis of the image (see FIG. 1).
b) Recording the high/low energy CT values of the calibration objects and the target object and averaging them in each object and/or in each XY section of each object.
c) Using the known properties of the calibration objects and their high/low energy CT values, solve the system of equations (2,3) for coefficients A, B, C, D, E, F.
d) Using the target object's high and low CT values and coefficients from Step c), calculate the target object's density and effective atomic number from equations (2, 3).
e) Calculate the density and effective atomic number logs by averaging the values of density and effective atomic number in each X-Y section of the scan.

Typically, steps b) and c) are performed for each section of the CT image parallel to the X-ray path (e.g., each X-Y section), and step d) is performed in each point (e.g. voxel) of the 3-D image, using coefficients determined for the corresponding X-Y section.

The problem with this approach is that the model determined by equations (2,3) does not account for all effects involved in the process of X-ray computed tomography. As a result, the density values obtained in step d) and averaged over the target object do not always match the object densities determined by direct physical measurement, mass divided by volume. An example using the traditional method for estimating bulk density and effective atomic number for a shale sample is shown in FIG. 2 and FIGS. 3a-b.

Calculated densities are mostly less than measured, with the error sometimes exceeding the typically acceptable level of 5%. There is no visible correlation between measured and calculated density values (correlation coefficient=−0.27).

In addition, the relationship between the effective atomic number and bulk density values calculated from dual energy method is very often difficult to explain by accepted rock physics models, which state that the rock density is, in general, increasing with the increase of the effective atomic number. See, for example, FIG. 3a) shows effective atomic number plotted versus bulk density values for a shale sample obtained by direct measurement, and exhibits in general an increase in the density when effective atomic number is increasing. The trend in FIG. 3b), displaying effective atomic number plotted versus calculated averaged bulk density shows an almost opposite trend. This effect was observed by Boyes (Boyes, J., "The Effect of Atomic Number and Mass Density on the Attenuation of X-rays," QUEEN'S HEALTH SCIENCES JOURNAL, 2003). On the other hand, the errors of effective atomic number are within acceptable limits. An example of a match between effective atomic number obtained from sample's mineral composition and effective atomic number estimated with the dual energy method is shown in FIG. 4.

Accordingly, the previous approaches to estimating density and/or effective atomic number of rock samples or well cores has shown to be not accurate enough to provide suitable information to the drilling and hydrocarbon recovery industry. There is a need for a more accurate method(s) to estimate effective atomic numbers and bulk densities of rock samples. Furthermore, a method for estimating effective atomic number and/or bulk density of rock samples needs to be provided that overcomes one or more of the above-identified problems.

SUMMARY OF THE INVENTION

A feature of the present invention is to provide an improved method to estimate the effective atomic number and bulk density of rock samples using X-ray computed tomographic imaging.

A further feature of the present invention is to provide a method to reduce the error between bulk density as measured in a physical laboratory and estimated bulk density by creating an error correction that is a function of the effective atomic number.

A further feature of the present invention is to generate trends of effective atomic number and estimated bulk density which are consistent with the expected relationship between effective atomic number and bulk density.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

To achieve these and other advantages, and in accordance with the purposes of the present invention, as embodied and broadly described herein, the present invention relates to a method to estimate the effective atomic number and/or bulk density of a target object or target objects. The target object can be a well core or rock sample or porous body or other object that can be scanned using an X-ray computed tomographic imaging device.

The method can include estimating the bulk density and/or effective atomic number of a target object. The method can involve one or more of the following steps:
i. performing a scan, such as a dual energy X-ray CT scan, of two or more reference objects and three or more calibration objects,
ii. obtaining a functional relationship between bulk density error and effective atomic number using scan values, such as CT values, from the reference objects and the calibration objects,
iii. performing a scan, such as a dual energy X-ray CT scan, of the target object and the three or more calibration objects,
iv. obtaining uncorrected density (e.g., $\rho_C^T$) and effective atomic number (e.g., $Z^T$) for the target object,
v. obtaining bulk density corrections using the functional relationship between bulk density error and effective atomic number from the reference objects and the effective atomic number (e.g., $Z^T$) for the target object, and
vi. obtaining the corrected bulk density using the bulk density corrections.

In addition, the present invention relates to a method for estimating the bulk density and/or effective atomic number of a target object which can achieve a density error less than methods described in the prior art. Density errors of 2% or less between the calculated density (e.g., bulk density) and the measured density (e.g., bulk density) have been observed in core samples.

The present invention further relates to a method for estimating the bulk density of a target object such that the correlation coefficient between the calculated density and the measured density is higher than correlation coefficients produced by methods described in the prior art. Correlation coefficients in core samples have been observed at least 0.7 and higher, such as 0.87 or more.

It is to be understood that both the foregoing general description and following detailed description are exemplary and explanatory only and are intended to provide a further explanation of the present invention, as claimed.

The accompanying drawings, which are incorporated in and constitute a part of this application, illustrate features of the present invention and together with the description, serve to explain the principles of the present invention.

DETAILED DESCRIPTION OF THE PRESENT INVENTION

Figure 1:
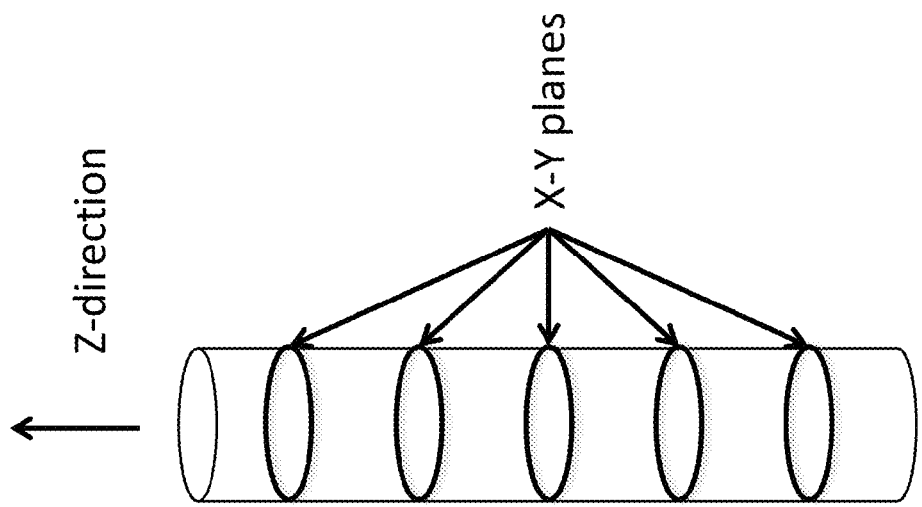
FIG. 1 is a perspective view of a core sample and the coordinate system used to reference the core.

The present invention relates to methods to estimate the bulk density and/or effective atomic number of a target object. The target object can be a rock sample, or well core sample, or porous body, or any other object that requires an estimation of bulk density and/or effective atomic number. The target object is generally a solid. The target object could be a liquid or contain a liquid. The target object can be an object received from a drilling site, proposed drilling site, subterranean site, or above-ground site, or any other location wherein a sample can be retrieved and wherein the bulk density and/or effective atomic number needs to be estimated. A series of two or more target objects can be processed in the methods of the present invention.

The method for estimating the bulk density and/or effective atomic number of a target object can involve one or more of the following steps which can be performed once or multiple times:

i. performing a scan (such as a dual energy X-ray CT scan) of two or more reference objects and three or more calibration objects, ii. obtaining a functional relationship between bulk density error and effective atomic number using scan values (e.g., CT values) from the reference objects and the calibration objects, iii. performing a scan (such as a dual energy X-ray CT scan) of the target object and the three or more calibration objects, iv. obtaining uncorrected density (e.g., $\rho_C^T$) and effective atomic number (e.g., $Z^T$) for the target object, v. obtaining bulk density corrections using the functional relationship between bulk density error and effective atomic number, and the effective atomic number, $Z^T$, for the target object, and vi. obtaining the corrected bulk density using the bulk density corrections.

The description below uses a complete well core sample (e.g. whole core or round core) as an example of the target object, but it is to be understood that the methods described herein apply not only to whole core samples but to slabbed cores, cut or sliced cores, rock samples generally and to porous bodies in general and, as indicated above, to target objects in general.

The root of the described problem is in the simplicity of the model expressed by equations (2,3). This model does not take into account the polychromatic nature of the X-ray energy in the medical scanners used for scanning rock samples such as whole cores using X-ray CT scanning. In reality, the presence of the core inside the scanner changes not only the intensity of the X-rays (which is in general compensated by the CT reconstruction algorithms), but also their spectrum. The change of the spectrum is most strongly affected by the core's effective atomic number. The effect may also change with the core size (diameter), the size, and location of calibration objects, and other elements in the scanner including the age of the scanner.

The present invention is unique in that it utilizes the observation that the change of the spectrum is most strongly affected by the core's effective atomic number and then correlating the error in the average calculated core density values with core's average calculated effective atomic number, and applying the error correction to all calculated density/effective atomic number pairs. This produces the unexpected result that the estimated values of averaged calculated bulk density are well correlated with measured bulk density, and the trend of estimated bulk density and effective atomic number matches the trends observed in laboratory experiments.

The present invention has the ability to improve the estimate of the bulk density of a target object such that the calculated bulk density is closer to the measured density of the same target object using method described in the prior art. This is considered the density error (between the calculated bulk density and measured bulk density). Density errors of less than 10%, less than 5%, less than 2% and lower have been observed. This density error can be the difference between the average of calculated densities and measured densities of the target object and/or can be based on each individual point or scan. The present invention can provide a correlation coefficient (between the calculated density and measured density) of at least 0.7. A perfect correlation between the calculated density and measured density of the same target object would be 1.0. The correlation coefficient between the calculated density and measured density can be at least 0.75, at least 0.8, at least 0.85, at least 0.9, at least 0.925, at least 0.95, or greater. This again can be an average of readings and/or based on each individual point/reading or scan. The correlation coefficient can be determined as follows:

$$r = \frac{1}{n} \sum_{i=1}^{n} \left(\frac{X_i - \overline{X}}{S_X}\right)\left(\frac{Y_i - \overline{Y}}{S_Y}\right)$$

where
n=number of samples
and are sample means
s=standard deviation.

With regard to the two or more reference objects, these objects can be rock samples, well core samples, partial well core samples, or other objects that have a known bulk density. Each of the reference objects has a different effective atomic number and/or bulk density from each other. With regard to the three or more calibration objects, these objects can be liquid or solid materials such as polymers, metals, minerals or chemical compounds. Each of the calibration objects has a different effective atomic number and/or bulk density from each of the other calibration objects.

Figure 7:
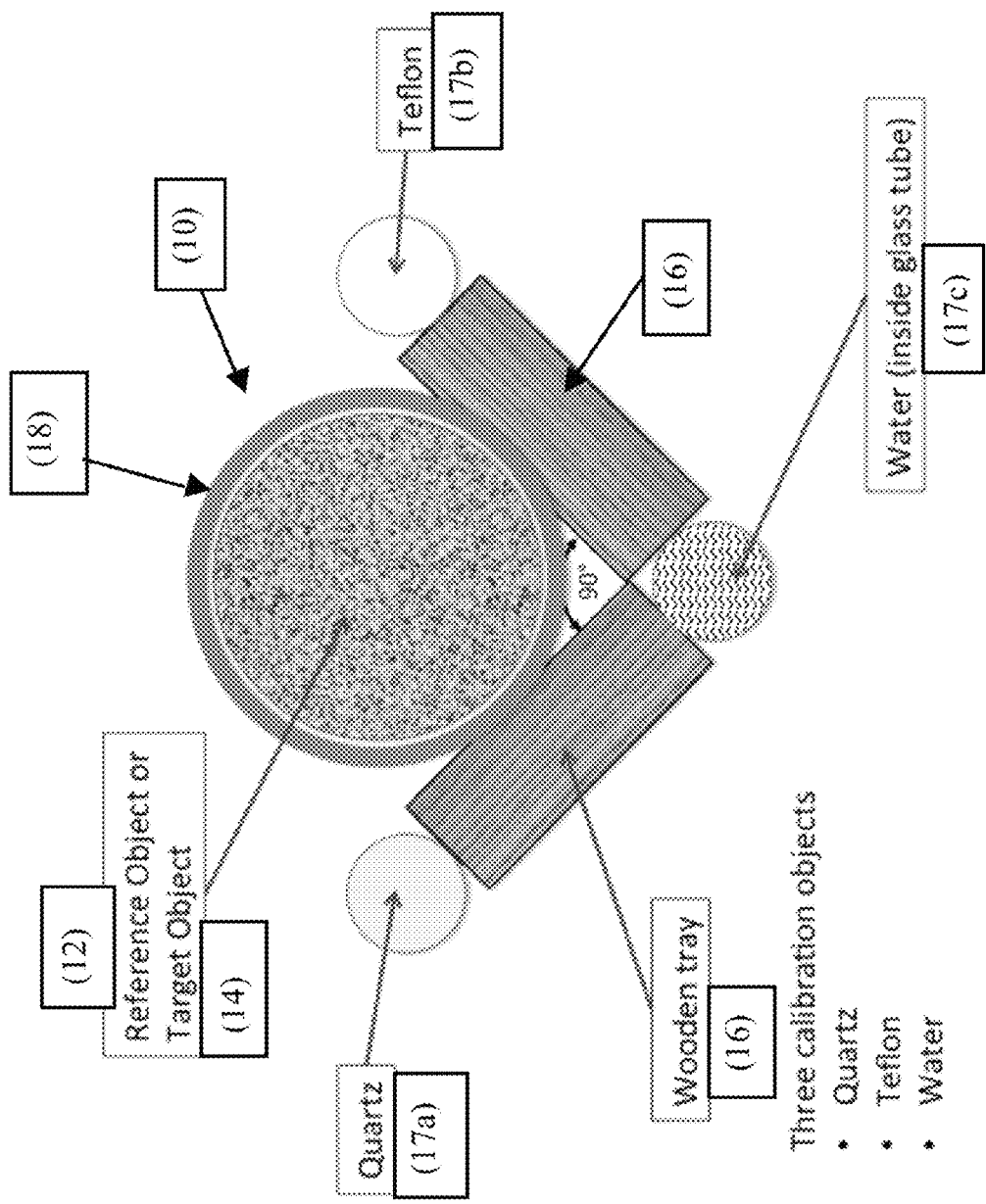
FIG. 7 is a pictorial drawing (not to scale) of one example of the arrangement of the reference object or target object in association with the calibration objects and tray of the scanner.

With regard to the scan of the objects involved in the method of the present invention, the scan can be accomplished using a scanner, such as a dual energy scanner (for instance, a dual energy X-ray CT scanner). One device that can be used that is commercially available is a CereTom™ Scanner. The scanner itself can move to scan the target object, reference objects, and calibration objects. In the alternative, the objects being scanned can move through a stationary scanner. Either option is possible. Regarding the arrangement of objects, FIG. 7 shows one example of such an arrangement. The overall arrangement of objects, 10 is shown. Reference object 12 or target object 14 can be located on a tray 16, for instance, a wooden tray, which has left side and right side. The reference object or target object can rest on this tray. In addition, the three calibration objects, 17a, 17b, and 17c, can be located adjacent to the reference object 12 or target object 14 in any arrangement. The calibration objects 17a-17c can be in contact with the target object 14 or reference object 12 or there can be any amount of space between the calibration objects and reference objects or target object. The calibration objects 17a-17c can be attached or otherwise held in place by the tray 16. In the example, the three calibration objects are quartz (17a), Teflon (17b), and water (17c), which is within a glass tube. The three calibration objects can surround the reference object or target object in a clockwise fashion around the reference object or target object. In the alternative, the calibration objects can have any spatial relationship to the reference object or target object. Thus, calibration objects can surround the target object or reference object or be on one side of the target object or reference object, or in any other arrangement.

Generally, one reference object or the target object is scanned at a time. As an option, the target object, along with one or more reference objects or several reference objects, can be scanned at the same time in series by placing them sequentially in series on the tray. The reference objects and/or target object can be placed in a holder, such as a metal holder (for instance, a circular tube) that rests on the tray. As shown in FIG. 7, the circular tube 18 can contain the reference object or target object and can rest on tray 16. Examples of materials that can be used include, but are not limited to, aluminum, aluminum alloys, plastics and the like. There is no criticality with regard to the arrangement of the reference object, target object, calibration objects, or additional optional components that are used to hold these various objects. However, the arrangement of all objects during the scan of the target objects must be the same as the arrangement during scanning of the reference objects. The spacing between the three or more calibration objects can be any distance, for instance, there can be a space of from 0.1 cm to 10 cm, for instance, 1 cm to 5 cm, and the like, from each calibration object.

With regard to the calibration objects, the calibration objects can be different or the same with respect to size and/or shape to each other. The calibration objects have sufficient voxels in each cross-section of each calibration object for efficient averaging of the scanned values. For instance, each calibration object can have 300 voxels per section that is scanned or more, such as 300 voxels to about 1000 voxels per scanned section or more. More specific examples include from 400 voxels to 500 voxels or 400 voxels to 1000 voxels, or 600 voxels to 1000 voxels per scanned section. The calibration objects, as stated, can have any shape or size and, for instance, can be circular, semi-circular, rectangular, or have other geometric shapes. For instance, the diameter, if the calibration object is semi-circular or circular can be from 1 to 5 cm, for instance, from 2 to 4 cm.

Further, each calibration object can vary in shape and/or size from each other. Preferably, the calibration object does have a uniform size and shape and, more preferably, the calibration objects each have a similar size and shape, but this is not required. The calibration objects should have sufficient length so that the calibration object is always part of any scanning of the reference object(s) and/or the target object. Accordingly, for purposes of the present invention, the calibration objects have a length that is equal to or greater than the length of the reference object and the length of the target object.

Generally, the preferred calibration objects are selected in order to span the expected effective atomic number of the target object. Thus, one or more of the calibration objects can be a sort of "end point," so that the expected effective atomic number of the target object can fall in between the one or more calibration objects' effective atomic number. Generally, though not required, each calibration object will have an effective atomic number and/or bulk density that is at least 10% different from each other.

Examples of the calibration object materials include, but are not limited to, water (which can be placed in a glass tube), glass, quartz, Teflon, other polymeric materials, other mineral-based materials, other liquid base materials, and the like. As long as the density and effective atomic number of the calibration object is known and the calibration objects do not include elements in which the ratio of atomic weight to atomic number is greater than about 2.1, the objects can serve as calibration objects in the present methods. The calibration objects should be homogeneous at the level of resolution of the scan, which typically is less than 0.2 mm. As a further example, calibration objects are homogenous materials at a level of resolution of from 0.2 mm or less, such as 0.1 mm or less, or 0.05 mm or less, such as 0.01 to 0.1 mm, or 0.001 mm to 0.1 mm.

When a method for estimating the bulk density and effective atomic number of a target object is done, the same calibration objects are used during the scanning of the reference objects and the target object.

With regard to the reference objects, the reference objects generally have the same or similar cross-section in size and shape to each other. Further, the reference objects have similar or the same cross-section in size and shape to the target object, and are placed in the same or similar object holder, if any is used for the target object. For instance, if the target object is round, then the reference object should be round or approximately round with a same cross-sectional area or similar cross-sectional area. As a further example, the reference objects and target object should have a cross-sectional area that is within about 10% of each other, within 5% of each other, within 1% of each other, or within 0.5% of each other. As indicated above, the reference objects and the target object do not need to be similar in size or shape to the calibration objects. Examples of reference objects include, but are not limited to, any object that has a known bulk density, such as Berea Sandstone. With regard to the reference object, only the bulk density needs to be known with regard to each reference object. As an option, the effective atomic number of one or more of the reference objects can also be known.

The reference objects can be circular, semi-circular, rectangular, or have other geometrical shapes. For instance, in the case of cylindrical objects, the reference objects and target objects can have a diameter of from 5 cm to 15 cm, and can be of any length, such as from 50 cm to 500 cm or longer, for instance, 1 to 200 cm in length.

The performing of the dual energy X-ray CT scan of the two or more reference objects and three or more calibration objects can occur in the same CT scan or can occur in multiple scans. Generally, the same CT scan device with the same settings is used if multiple scans are used. Examples of obtaining or determining the functional relationship between the bulk density error and effective atomic number from the CT values of the CT scan for the reference objects and calibration objects are exemplified below. Other functional relationships using similar calculated approaches can be performed.

It is possible to perform the CT scan for the target object and the reference objects in one combined CT scan or in multiple CT scans using any combination of objects to be scanned with the restriction that the calibration objects must be present in all scans. The obtaining of the uncorrected density and effective atomic number for the target object and obtaining the bulk density corrections are exemplified below. Other calculations and determinations can be used, as well.

The present invention relates to a method for estimating the bulk density and/or effective atomic number of a target object. This method of estimating involves the use of a scanner (e.g., dual-energy X-ray CT scanner) and the related determinations can be performed by programs that are present on one or more computer devices or can be installed within the scanner (e.g., CT scanner) itself. For purposes of the present invention, the various steps of obtaining the functional relationship can be performed in one or more computer programs and stored in a computer or separate hard drive or other memory device. It is to be understood that the methods of the present invention are considered part of the present invention, as well as the results from performing the method, including the corrected bulk density and bulk density correction values obtained. Accordingly, the present invention relates to computers, memory devices that contain the programs that permit the method for estimating the bulk density and/or effective atomic number.

The correlation between the errors of density values and calculated effective atomic number may be different for different scanners, target object size and location within the scanner, relative position of the calibration objects and the sample, but is independent of the other properties of the target and reference objects such as chemical composition, porosity and fluid content, as these are fully accounted for by the object's effective atomic number and density. The correlation between the errors of density values and calculated effective atomic number can take many forms such as linear, polynomial, exponential and others. Two examples of the correlation are as follows:

1. Linear correlation of absolute errors of the density with effective atomic number, and
2. Linear correlation of relative errors of the density with effective atomic number.

Those skilled in the art will recognize that the methods described herein are suitable for other types of correlations between errors in density values and effective atomic number.

The relative error, $\epsilon$, of the averaged density values can be expressed as a linear function of the effective atomic number:

$$\epsilon = aZ + b \quad (4)$$

where $$\varepsilon = \frac{(\rho_c - \rho_0)}{\rho_0} = \text{the relative error of average density,}$$

$\rho_c$ is the average density calculated by dual energy method,
$\rho_0$ is the measured density of the rock sample,
$Z$ = effective atomic number,
a and b are constants.

Once the correlation is established for a given scanning configuration (scanner, core size and location, core barrel, etc.), it is used to correct the density values by predicting the relative error from the target object's Z values by using equation 4, and then calculating the true density, $\rho'_c$, as $$\rho'_c = \frac{\rho_c}{1 + \varepsilon}. \quad (5)$$

The absolute error, $\delta$, of the averaged density values can be expressed as a linear function of the effective atomic number:

$$\delta = cZ + d \quad (6)$$

where
$\delta = \rho_c - \rho_o$ = the absolute error of density,
$\rho_c$ is the average density calculated by dual energy method,
$\rho_o$ is the measured density of the rock sample,
$Z$ = effective atomic number,
c and d are constants.

Once the correlation is established for a given scanning configuration (scanner, core size and location, core barrel, etc.), it is used to correct the density values by predicting the relative error from the core's Z values by using equation (6), and then calculating the true density as $$\rho'_c = \rho_c - \delta \quad (7).$$

Both of these correlations and, optionally, other correlations can be determined. As an option, one can be selected based on minimization of the density error after applying the correction. The density correction can be applied to each voxel in the 3D image, to the average of the voxels in each X-Y plane, the average of all the voxels in the entire sample, or other subsamples of the whole sample.

The present invention is applicable in cases where distributions of density and effective atomic number values are obtained in each of a plurality of samples or in each of a plurality of locations within a sample, such as cores of similar geometry (shape and size of cross-section).

The improved method for estimating density and effective atomic number of a target object sample can comprise the following steps (steps I and II may be performed in any order):

I. Calculate a functional relationship between bulk density error and effective atomic number as follows:

i. Acquire a set of at least five objects with known density. At least two of these known objects match the scan geometry (target object size) and are designated as the reference objects and have different densities and chemical composition. At least three of the five objects are designated as calibration objects, and are generally homogeneous and made of materials with known and different densities and effective atomic numbers. The calibration objects must be at least as long as the reference objects and target objects such that the calibration objects are always in the field of the X-rays when the target object or reference objects are in the field of the X-rays. Reference objects, as used here, can refer to whole cores, fragments of whole cores, or objects manufactured for this purpose. The density and effective atomic number values of the reference objects should cover the expected range of densities and effective atomic numbers in the target object under investigation.

ii. Calculate the uncorrected density, $\rho_c^R$ and effective atomic number, $Z^R$, for the reference objects as follows.

a. The reference objects and calibration objects are simultaneously imaged in an X-ray CT scanner, such as a CereTom GEO scan model number NL3100, CereTom OTO scan model number NL3100, or a similar-ray CT scanner.

b. Record the high CT value, $CTH_v^R$, and low CT value, $CTL_v^R$, for each voxel in the reference objects. In the case of cores, the core axis is aligned with the Z axis of the image (see FIG. 1).

c. Record the high CT value, CTH, and the low CT value, CTL, for each voxel of each of the calibration objects, $CTH_v^C$ and $CTL_v^C$, and average them over all of the voxels in each X-Y plane of each of the calibration objects, $CTH_{X-Y}^C$ and $CTL_{X-Y}^C$.

d. Use the known bulk density, $\rho_0^C$, and effective atomic number, $Z_0^C$, of at least three of the calibration objects and their respective CT values, $CTH_{X-Y}^C$ and $CTL_{X-Y}^C$, to solve the system of equations (8,9)

$$\rho_0^C = A*CTH_{X-Y}^C + B*CTL_{X-Y}^C + C \quad (8)$$

$$\rho_0^C (Z_0^C)^\alpha = D*CTH_{X-Y}^C + E*CTL_{X-Y}^C + F \quad (9)$$

for coefficients A, B, C, D, E, F. The value of the exponent a may be 2.98, 3.6, 3.8, 4.0 or other values. For rock samples a value of $\alpha=3.8$ is preferred. If the system of equations is over-specified, a least squares or other method may be used to determine the best or optimum values of the coefficients A, B, C, D, E, F.

e. Using $CTH_v^R$, and $CTL_v^R$ values from the reference objects and coefficients (A, B, C, D, E, F) from step I-ii-d above, calculate the reference objects' density and effective atomic number for each voxel in the reference objects, $\rho_v^R$ and $Z_v^R$, from equations (10,11)

$$\rho_v^R = A*CTH_v^R + B*CTL_v^R + C \quad (10)$$

$$\rho_v^R(Z_v^R) = D*CTH_v^R + E*CTL_v^R + F \quad (11).$$

iii. For each reference object, n, average the values of $\rho_v^R$ and $Z_v^R$. The averages, $\rho_{avg}^R$ and $Z_{avg}^R$, are calculated. The averaging can be performed over the whole volume of the reference object, or over a selected portion of it, free of the boundary effects of the scan. The preferred method is to average the CT values for each slice in the reference object, n, and then calculate bulk density and effective atomic number for each slice directly from the average CT values, and then average the density and effective atomic number of slices.

iv. For each reference object, n, measure its mass and volume and calculate the measured average bulk density, $\rho_0^R$, as a ratio of mass over volume.

v. For each reference object, n, compute the absolute error in density, $\delta$, and the relative error in density, $\epsilon$, from $$\delta = \rho_{avg}^R - \rho_0^R \quad (12)$$

$$\varepsilon = \frac{\rho_{avg}^R - \rho_0^R}{\rho_0^R}. \quad (13)$$

vi. Determine a functional relationship between $\epsilon$ and the effective atomic number, Z, by solving the following system of equations (14) for a and b $$\epsilon(1) = a*Z_{avg}^R(1) + b \quad (14a)$$

$$\epsilon(2) = a*Z_{avg}^R(2) + b \quad (14b)$$

$$\epsilon(n) = a*Z_{avg}^R(n) + b \quad (14c)$$

where
$\epsilon(n)$=relative error of density for reference object n,
$Z_{avg}^R(n)$ calculated average effective atomic number for reference object n,
a and b are constants.

If the system of equations (14) is over-specified, a least squares or other method may be used to determine the best or optimum values of the coefficients a and b.

vii. Determine a functional relationship between $\delta$ and the effective atomic number, Z, by solving the following system of equations (15) for a and b $$\delta(1) = c*Z_{avg}^R(1) + d \quad (15a)$$

$$\delta(2) = c*Z_{avg}^R(2) + d \quad (15b)$$

$$\delta(n) = c*Z_{avg}^R(n) + d \quad (15c)$$

where
$\delta(n)$=relative error of density for reference object n,
$Z_{avg}^R(n)$=calculated average effective atomic number for reference object n,
a and b are constants.

If the system of equations (15) is over-specified, a least squares or other method may be used to determine the best or optimum values of the coefficients c and d.

II. Calculate the uncorrected density, $\rho_c^T$, and effective atomic number, $Z^T$, for the target object as follows:

i. The target object and calibration objects are simultaneously imaged in an X-ray CT scanner, such as Cere-Tom™ GEO scan model number NL3100, Cere-Tom™ OTO scan model number NL3100, or a similar-ray CT scanner using the same geometrical arrangement of objects as in step I.ii.a above. The calibration objects used here are the same calibration objects as used in I-i above. In the case of cores, the core axis is aligned with the Z axis of the image (see FIG. 1).

ii. Record the high CT value, $CTH_v^T$, and low CT value, $CTL_v^T$, for each voxel in the target object. In the case of cores, the core axis is aligned with the Z axis of the image (see FIG. 1).

iii. Record the high CT value, $CTH_v^C$, and the low CT value, $CTL_v^C$, for each voxel of each of the calibration objects and average them over all of the voxels in each X-Y plane of each of the calibration objects, $CTH_{X-Y}^C$ and iv. Use the known bulk density, $\rho_0^C$, and effective atomic number, $Z_0^C$, of the calibration objects and the CT values $CTH_{X-Y}^C$ and $CTL_{X-Y}^C$ to solve the system of equations (16, 17) in each X-Y plane of the scan:

$$\rho_0^C = G*CTH_{X-Y}^C + H*CTL_{X-Y}^C + J \quad (16)$$

$$\rho_0^C(Z_0^C)^\alpha = K*CTH_{X-Y}^C + L*CTL_{X-Y}^C + M \quad (17)$$

for coefficients G, H, J, K, L, M. If the system of equations is over-specified, a least squares or other method may be used to determine the best or optimum values of the coefficients G, H, J, K, L, M.

v. Use CT values from the target object, $CTH_v^T$, and $CTL_v^T$, and coefficients (G, H, J, K, L, M) from step II-iv above, to calculate the target object's density, $\rho_v^T$, and effective atomic number, $Z_v^T$, for each voxel in the target object, from equations (18, 19):

$$\rho_v^T = G*CTH_v^T + H*CTL_v^T + J \quad (18)$$

$$\rho_v^T*(Z_v^T)^\alpha = D*CTH_v^R + E*CTL_v^R + F \quad (19).$$

III. For each voxel in the target object, calculate the relative error in density, $\epsilon_v^T$, from equation (20)

$$\epsilon_v^T = a*Z_v^T + b \quad (20)$$

where a and b are coefficients calculated from step I-vi above.

IV. For each voxel in the target object, calculate the absolute error in density, $\epsilon_v^T$, from equation (21)

$$\delta_v^T = c*Z_v^T + d \quad (21)$$

where c and d are coefficients calculated from step I-vii above.

V. Calculate corrected bulk density values, $\rho_v^{T\epsilon}$, by applying the relative error correction factors, $\epsilon_v^T$, to the calculated density values, $\rho_v^T$, using equation (22):

$$\rho_v^{T\varepsilon} = \frac{\rho_v^T}{1+\varepsilon_v^T}. \quad (22)$$

VI. Calculate corrected bulk density values, $\rho_v^{T\delta}$, by applying the absolute error correction factors, $\delta_v^T$, to the calculated density values, $\rho_v^T$, using equation (23):

$$\rho_v^{T\delta} = \rho_v^T - \delta_v^T \quad (23).$$

VII. Either $\rho_v^{T\epsilon}$ or $\rho_v^{T\delta}$ may be used as an improved estimate of bulk density based on choosing the model giving the least average error in bulk density.
VIII. Optionally, either $\rho_v^{T\epsilon}$ or $\rho_v^{T\delta}$ may be averaged over the voxels in each X-Y plane of the target object to produce a bulk density log.
IX. Optionally, $Z_v^T$ may be averaged over the voxels in each X-Y plane of the target object to produce an effective atomic number log.
X. Optionally, either $\rho_v^{T\epsilon}$ or $\rho_v^{T\delta}$ may be averaged over all the voxels in the entire target object to produce an average bulk density for the entire target object.
XI. Optionally, both $\rho_v^{T\epsilon}$ or $\rho_v^{T\delta}$ may be averaged using simple or weighted averages to produce density logs or average bulk density values.
XII. Optionally, calculate the standard deviation, $\sigma_\epsilon$, of the differences between the average corrected calculated bulk density using relative error correction and the average physically measured bulk density, $\rho_{avg}^{R\epsilon}-\rho_0^R$, for every reference object. Calculate the standard deviation, $\sigma_\delta$, of the differences between average corrected calculated bulk density using absolute error correction and the average physically measured bulk density, $\rho_{avg}^{R\delta}-\rho_0^R$, for every reference object. The correction method, absolute or relative, with the lowest standard deviation, $\sigma_\epsilon$ or $\sigma_\delta$, is used to estimate the corrected bulk density of the target object.

Figure 8:
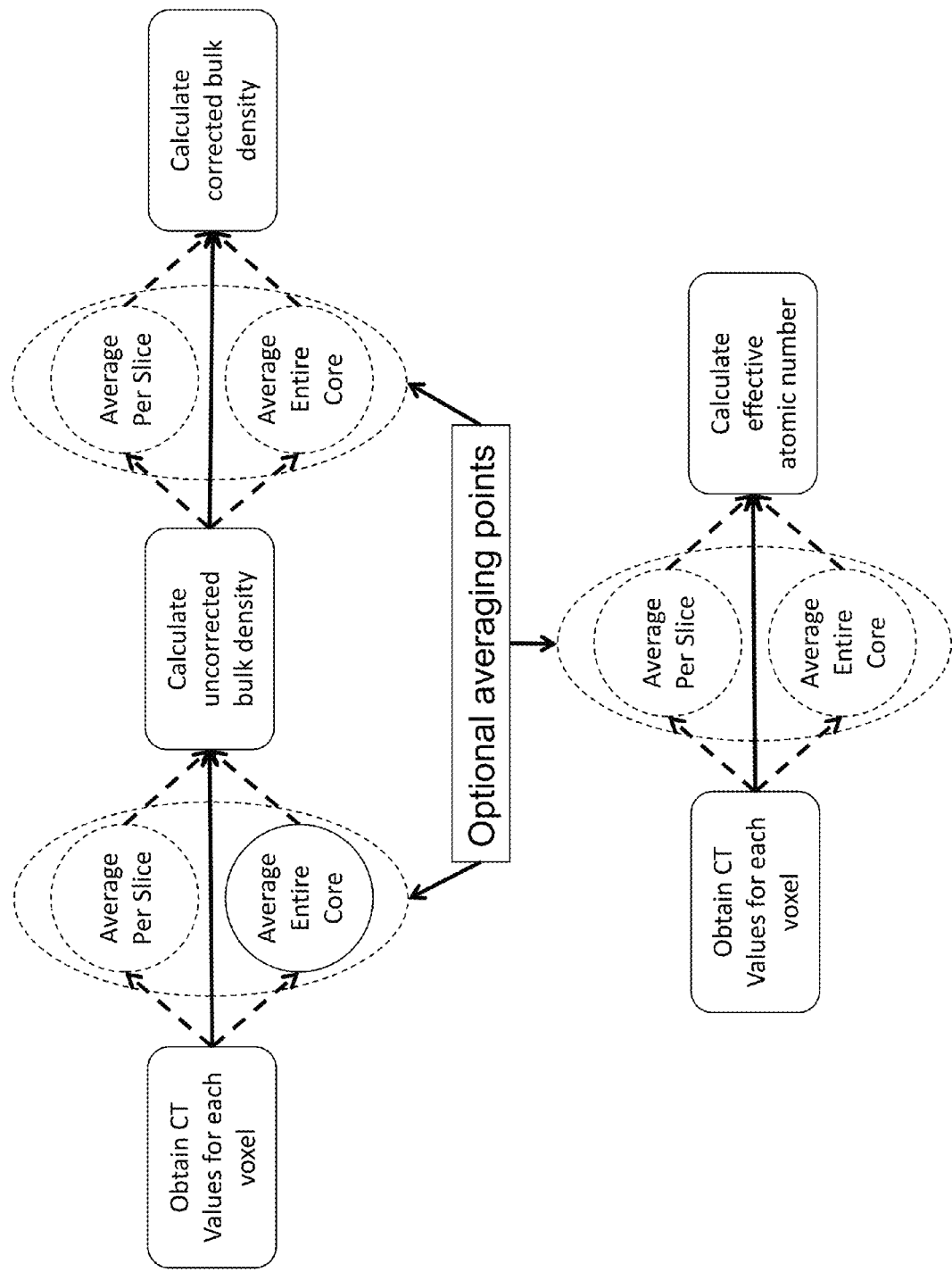
FIG. 8 is a flow chart showing various methods for calculating average values of bulk density and effective atomic number.

There are several optional methods that can be applied to calculate average corrected bulk density and average effective atomic number for each slice in a target object (core) or for the entire target object (core). Averaging may be performed at the level of CT values, uncorrected bulk density or corrected density to estimate average corrected bulk density. Similarly, averaging may be performed at the level of CT values or effective atomic number to estimate average effective atomic number. FIG. 8 shows these options diagrammatically.

The present invention includes the following aspects/embodiments/features in any order and/or in any combination:

1. The present invention relates to a method for estimating the bulk density and/or effective atomic number of at least one target object comprising:
   i. performing a scan of two or more reference objects and three or more calibration objects,
   ii. obtaining a functional relationship between bulk density error and effective atomic number using scan values from the reference objects and the calibration objects,
   iii. performing a scan of the target object and the three or more calibration objects,
   iv. obtaining uncorrected density and effective atomic number for the target object,
   v. obtaining bulk density corrections using the functional relationship between bulk density error and effective atomic number from the reference objects, and the effective atomic number for the target object, and
   vi. obtaining the corrected bulk density using the bulk density corrections.
2. The method of any preceding or following embodiment/feature/aspect, wherein the target object is a porous body.
3. The method of any preceding or following embodiment/feature/aspect, wherein the target object is a rock sample.
4. The method of any preceding or following embodiment/feature/aspect, wherein the target object is a well core.
5. A method for estimating the bulk density of a target object comprising determining a bulk density error function from a set of objects with known bulk density and/or effective atomic number and then using the bulk density error function to adjust the uncorrected estimate of bulk density of an object with unknown bulk density and atomic number.
6. The method of any preceding or following embodiment/feature/aspect, wherein said target object is a solid.
7. The method of any preceding or following embodiment/feature/aspect, wherein the target object is a liquid or comprises a liquid.
8. The method of any preceding or following embodiment/feature/aspect, wherein said target object is obtained from a drilling site, proposed drilling site, subterranean site, or above-ground site.
9. The method of any preceding or following embodiment/feature/aspect, wherein said scan is a CT scan.
10. The method of any preceding or following embodiment/feature/aspect, wherein said scan is a dual-energy X-ray CT scan.
11. The method of any preceding or following embodiment/feature/aspect, wherein said two or more reference objects are rock samples, well core samples, partial well core samples, or other objects having a known bulk density.
12. The method of any preceding or following embodiment/feature/aspect, wherein said three or more calibration objects have a different effective atomic number and/or bulk density from each other.
13. The method of any preceding or following embodiment/feature/aspect, wherein at least one of the three or more calibration objects comprise a liquid.
14. The method of any preceding or following embodiment/feature/aspect, wherein at least one of the three or more calibration objects comprise a solid.
15. The method of any preceding or following embodiment/feature/aspect, wherein at least one of said three or more calibration objects is a mineral material, a polymer material, or an aqueous solution.
16. The method of any preceding or following embodiment/feature/aspect, wherein said calibration objects are quartz, Teflon, and water.
17. The method of any preceding or following embodiment/feature/aspect, wherein said scan is accomplished with a scanner, wherein said scanner moves to scan the target object, reference objects, and calibration objects.
18. The method of any preceding or following embodiment/feature/aspect, wherein said scan is accomplished with a scanner, wherein the target object, reference objects, and calibration objects move through a stationary scanner.
19. The method of any preceding or following embodiment/feature/aspect, wherein said reference objects and/or target object are located on a tray.
20. The method of any preceding or following embodiment/feature/aspect, wherein said calibration objects are located adjacent to the reference objects and/or target object.
21. The method of any preceding or following embodiment/feature/aspect, wherein said calibration objects are in contact with the target object and/or at least one reference object.
22. The method of any preceding or following embodiment/feature/aspect, wherein said calibration objects are located adjacent to the reference objects and/or target object, but not in contact with the reference objects or target object.

23. The method of any preceding or following embodiment/feature/aspect, wherein said calibration objects are attached or otherwise held in place by said tray.

24. The method of any preceding or following embodiment/feature/aspect, wherein said calibration objects are equally spaced around said reference objects or said target object.

25. The method of any preceding or following embodiment/feature/aspect, wherein said reference objects and said target object are scanned with the same scan.

26. The method of any preceding or following embodiment/feature/aspect, wherein said reference objects and said target object are scanned in series.

27. The method of any preceding or following embodiment/feature/aspect, wherein said one or more reference objects and said target object are scanned separately.

28. The method of any preceding or following embodiment/feature/aspect, wherein said calibration objects have sufficient voxels in each cross-section of each calibration object for efficient averaging of the scanned values.

29. The method of any preceding or following embodiment/feature/aspect, wherein each calibration object has 300 voxels or more per section that is scanned.

30. The method of any preceding or following embodiment/feature/aspect, wherein each calibration object has 400 voxels to 1,000 voxels per section that is scanned.

31. The method of any preceding or following embodiment/feature/aspect, wherein said calibration objects are circular or semi-circular.

32. The method of any preceding or following embodiment/feature/aspect, wherein each calibration object varies in shape and/or size from each other.

33. The method of any preceding or following embodiment/feature/aspect, wherein said calibration objects have a uniform size and shape with respect to each other.

34. The method of any preceding or following embodiment/feature/aspect, wherein said calibration objects have a sufficient length such that each calibration object is always part of any scan of said reference objects or said target object.

35. The method of any preceding or following embodiment/feature/aspect, wherein each of said calibration objects avoid elements having a ratio of atomic weight to atomic number of greater than 2.1.

36. The method of any preceding or following embodiment/feature/aspect, wherein each of said calibration objects are homogeneous at a level of resolution of said scan.

37. The method of any preceding or following embodiment/feature/aspect, wherein said each of said calibration objects are homogeneous at a level of resolution of 0.2 mm or less.

38. The method of any preceding or following embodiment/feature/aspect, wherein the same calibration objects are used during the scanning of the reference objects and target object.

39. The method of any preceding or following embodiment/feature/aspect, wherein the reference objects have a similar or same cross-section in size and shape to said target object.

40. The method of any preceding or following embodiment/feature/aspect, wherein said reference objects are circular or semi-circular.

41. The method of any preceding or following embodiment/feature/aspect, wherein steps i. and iii. can be performed in any order.

42. The method of any preceding or following embodiment/feature/aspect, wherein said uncorrected density and/or effective atomic number is based upon an average per slice of said scan of the target object.

43. The method of any preceding or following embodiment/feature/aspect, wherein the corrected bulk density is based upon an average per slice of said scan in view of said bulk density corrections.

44. The method of any preceding or following embodiment/feature/aspect, wherein said uncorrected density and/or effective atomic number is based upon an average of entire scan of the target object.

45. The method of any preceding or following embodiment/feature/aspect, wherein the corrected bulk density is based upon an average of entire scan in view of said bulk density corrections.

46. The method of any preceding or following embodiment/feature/aspect, wherein obtaining a functional relationship between bulk density error and effective atomic number using scan values from the reference objects and the calibration objects comprises
   i. scanning the reference objects and calibration objects in a X-ray CT scanner, and
   ii. recording the high and low CT values from the X-ray CT scans, and
   iii. averaging the high and low CT values in each X-Y plane of the reference objects and calibration objects, and
   iv. using the known bulk density and effective atomic number of the calibration objects and their respective CT values to calculate a functional relationship between bulk density error and effective atomic number.

47. The method of any preceding or following embodiment/feature/aspect, wherein the obtaining bulk density corrections using the functional relationship between bulk density error and effective atomic number from the reference objects, and the effective atomic number for the target object comprises an absolute bulk density correction and/or relative bulk density correction.

48. The method of any preceding or following embodiment/feature/aspect, wherein the obtaining corrected bulk density using the bulk density corrections comprises applying absolute bulk density correction and/or absolute bulk density correction.

49. A computer program product on a computer readable medium that performs one or more of the methods described in any of the methods in any preceding or following embodiments/features/aspects. The present invention also relates to a computer program, when performed on a controller in a computerized device provides one or more of any of the methods in any preceding or following embodiments/features/aspects. The computer program on a computer readable medium can be non-transitory and/or can exclude signals.

The present invention can include any combination of these various features or embodiments above and/or below as set forth in sentences and/or paragraphs. Any combination of disclosed features herein is considered part of the present invention and no limitation is intended with respect to combinable features.

The present invention will be further clarified by the following examples, which are intended to be exemplary of the present invention.

EXAMPLES

Figure 2:
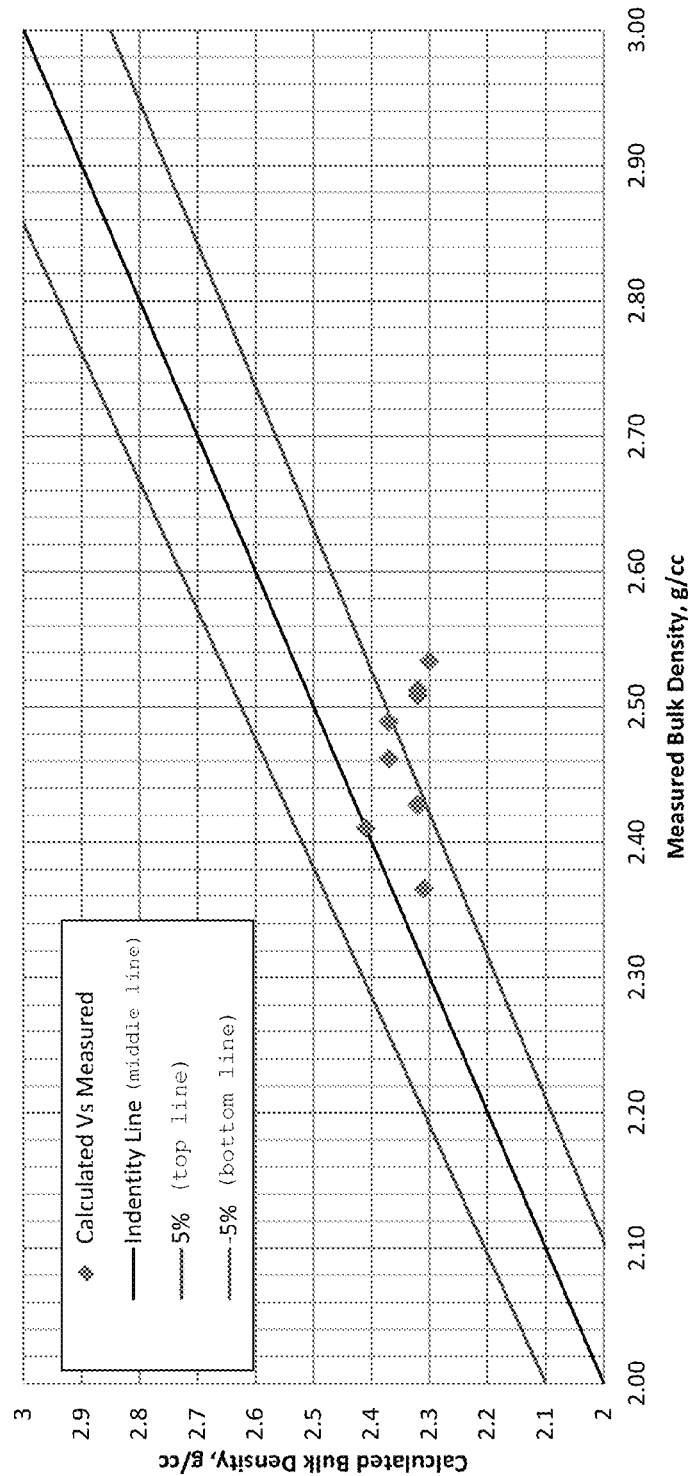
FIG. 2 is a graph that shows a typical comparison of shale core densities measured directly and calculated with the dual energy approach.
Figures 3A, 3B:
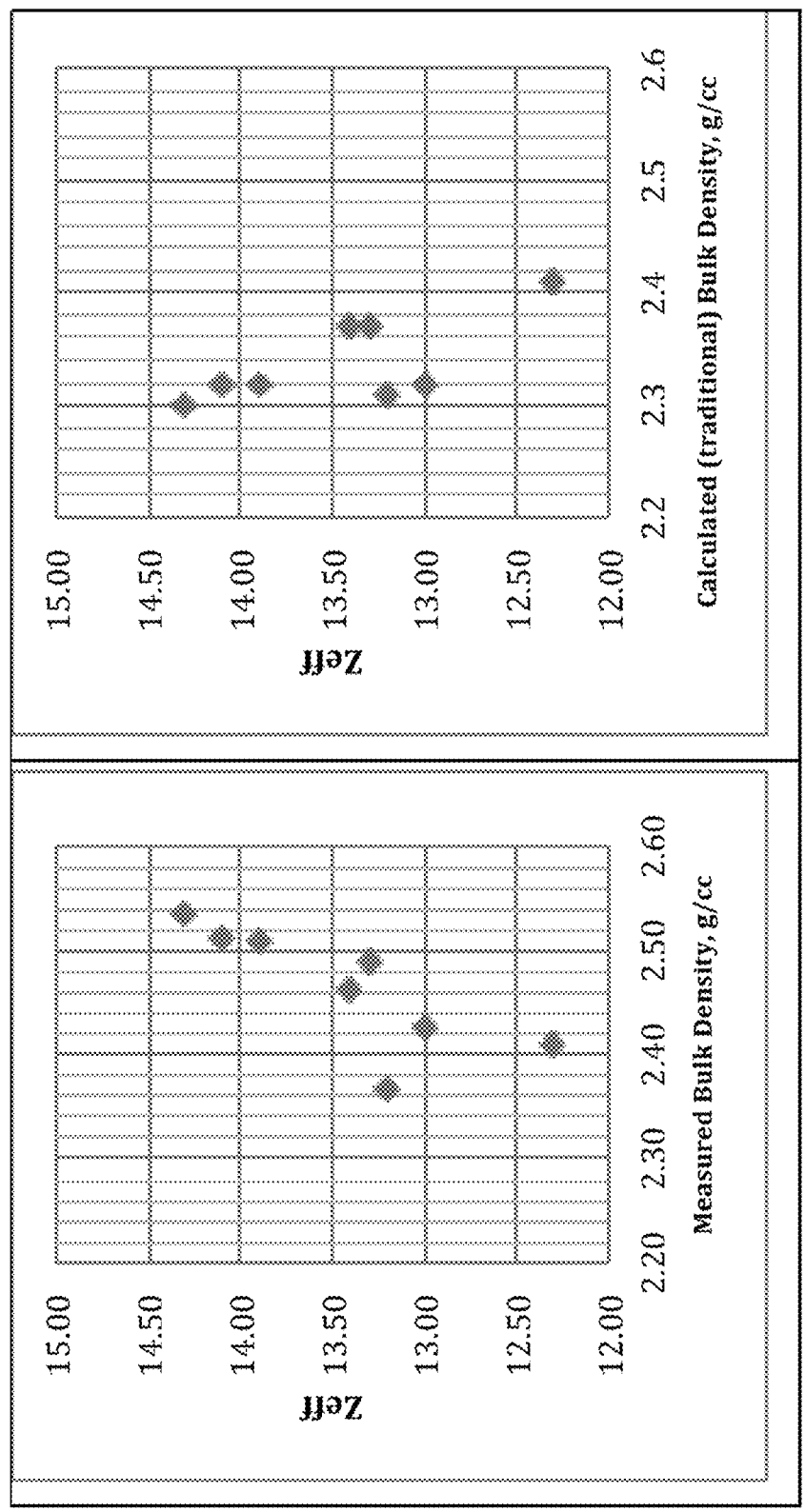
FIGS. 3a and 3b are graphs that show effective atomic number (Zeff) cross-plots versus measured (a) and calculated by a conventional method (b) bulk densities.
Figure 5:
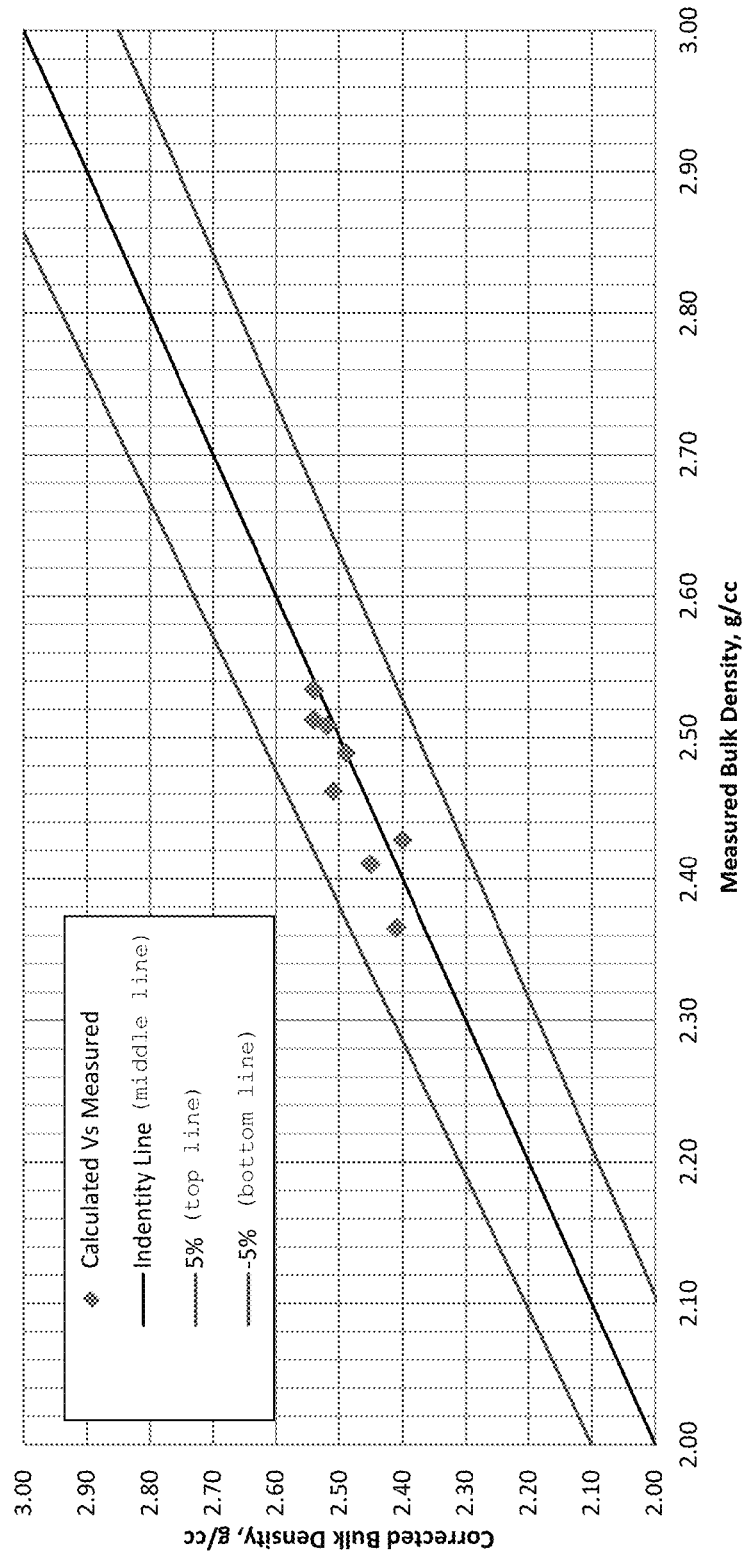
FIG. 5 is a graph that shows density estimated from dual energy X-ray CT using the proposed method (corrected density) versus measured density.
Figures 6A, 6B:
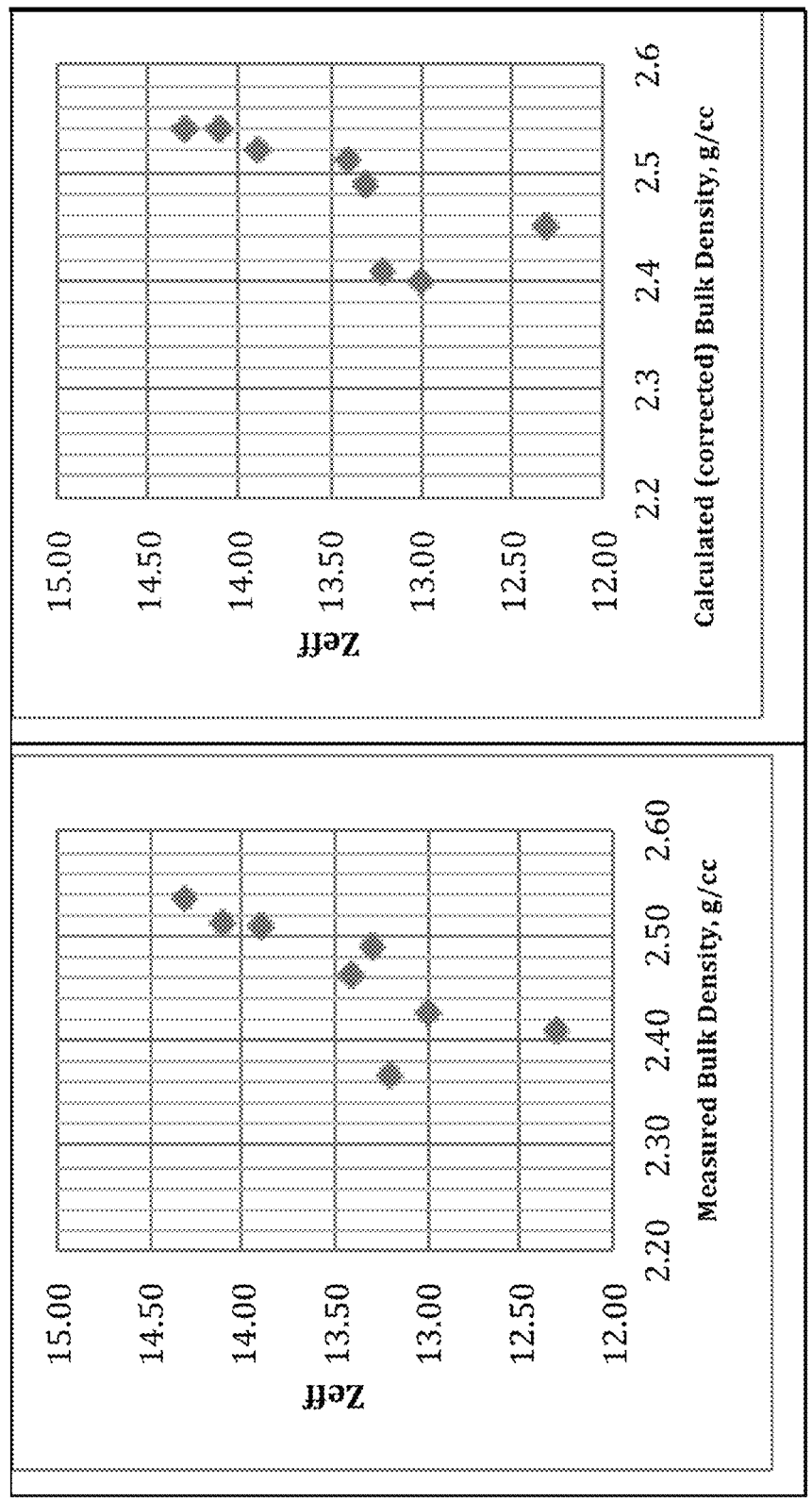
FIGS. 6a and 6b are graphs that show a comparison of Zeff/density trends for measured bulk density (a) and density calculated with the method of the present invention (b).

FIGS. 5 and 6*a-b* show the results of applying the method of the present invention to the same data as shown in FIGS. 2 and 3*a-b*. Not only is the density error small (never exceeding 2%), the two densities now correlate very well, with a correlation coefficient 0.87. The density/effective atomic number trends now also match expectations based on rock physics.

Figure 4:
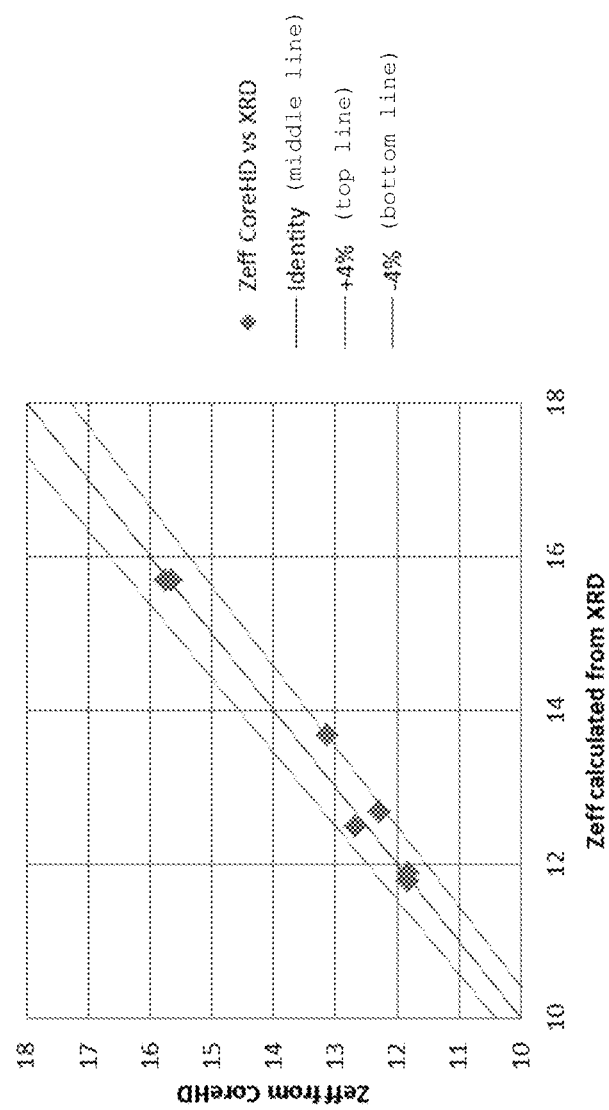
FIG. 4 is a graph that shows a comparison between effective atomic number obtained from mineralogy of various examples of sandstone, limestone, and dolomite rock samples and effective atomic number of the same samples calculated with the dual energy approach.

FIG. 4 is a graph showing an effective atomic number (Zeff) validation that shows a comparison between effective atomic number obtained from minerology ("COREHD") of the various examples of sandstone, limestone, and dolomite rock samples indicated in Table 1 and effective atomic number of the same samples calculated with the dual energy approach ("XRD"). The values of effective atomic number that were obtained or calculated in these respective manners are indicated in Table 1. In FIG. 4, the identity line is the solid line located between the +4% line that extends above it, and the −4% line that extends below it.

TABLE 1

| Material | Zeff from mineral composition (COREHD) | Zeff from Dual Energy Measurements (XRD) |
| --- | --- | --- |
| Buff Berea Sandstone | 11.8 | 11.8 |
| Crab Orchard Sandstone | 11.9 | 11.8 |
| Desert Pink Limestone | 15.7 | 15.8 |
| Edwards White Limestone | 15.7 | 15.6 |
| Idaho Sandstone | 12.5 | 12.7 |
| Silurian Dolomite | 13.7 | 13.1 |
| Scioto Sandstone | 12.7 | 12.3 |
| Comparison lines | 0 | 18 |
|  | 0 | 18.72 |
|  | 0 | 17.28 |

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A method for estimating the bulk density of at least one target object comprising:
   i. utilizing a scan of reference objects with known bulk density and calibration objects with known bulk density and effective atomic number,
   ii. obtaining a functional relationship between bulk density error and effective atomic number using scan values from the reference objects and the calibration objects,
   iii. utilizing a scan of the target object and the calibration objects,
   iv. obtaining uncorrected density and effective atomic number for the target object,
   v. obtaining bulk density corrections using the functional relationship between bulk density error and effective atomic number from the reference objects, and the effective atomic number for the target object, and
   vi. obtaining the corrected bulk density using the bulk density corrections.

2. The method of claim 1, wherein the target object is a porous body.

3. The method of claim 1, wherein the target object is a rock sample or a well core.

4. The method of claim 1, wherein the reference objects are two or more reference objects and the calibration objects are three or more calibration objects.

5. The method of claim 4, wherein said two or more reference objects are rock samples, well core samples, partial well core samples, or other objects having a known bulk density.

6. The method of claim 4, wherein said three or more calibration objects have a different effective atomic number and/or bulk density from each other.

7. The method of claim 4, wherein at least one of the three or more calibration objects comprise a liquid.

8. The method of claim 4, wherein at least one of the three or more calibration objects comprise a solid.

9. The method of claim 4, wherein at least one of said three or more calibration objects is a mineral material, a polymer material, or an aqueous solution.

10. The method of claim 4, wherein said calibration objects are quartz, Teflon, and water.

11. The method of claim 1, wherein said target object is a solid.

12. The method of claim 1, wherein the target object is a liquid or comprises a liquid.

13. The method of claim 1, wherein said target object is obtained from a drilling site, proposed drilling site, subterranean site, or above-ground site.

14. The method of claim 1, wherein said scans are a CT scan.

15. The method of claim 1, wherein said scans are a dual-energy X-ray CT scan.

16. The method of claim 1, wherein said scans are accomplished with a scanner, wherein said scanner moves to scan the target object, reference objects, and calibration objects.

17. The method of claim 1, wherein said scans are accomplished with a stationary scanner, wherein the target object, reference objects, and calibration objects move through the stationary scanner.

18. The method of claim 1, wherein said reference objects and/or target object are located on a tray.

19. The method of claim 18, wherein said calibration objects are attached or otherwise held in place by said tray.

20. The method of claim 1, wherein said calibration objects are located adjacent to the reference objects and/or target object.

21. The method of claim 1, wherein said calibration objects are in contact with the target object and/or at least one reference object.

22. The method of claim 1, wherein said calibration objects are located adjacent to the reference objects and/or target object, but not in contact with the reference objects or target object.

23. The method of claim 1, wherein said calibration objects are equally spaced around said reference objects or said target object.

24. The method of claim 1, wherein said reference objects and said target object are scanned in the same scan.

25. The method of claim 1, wherein said reference objects and said target object are scanned in series.

26. The method of claim 1, wherein said reference objects and said target object are scanned separately.

27. The method of claim 1, wherein said calibration objects have sufficient voxels in each cross-section of each calibration object for efficient averaging of the scanned values.

28. The method of claim 1, wherein each calibration object has 300 voxels or more per section that is scanned.

29. The method of claim 1, wherein each calibration object has 400 voxels to 1,000 voxels per section that is scanned.

30. The method of claim 1, wherein said calibration objects are circular or semi-circular.

31. The method of claim 1, wherein each calibration object varies in shape and/or size from each other.

32. The method of claim 1, wherein said calibration objects have a uniform size and shape with respect to each other.

33. The method of claim 1, wherein said calibration objects have a sufficient length such that each calibration object is always part of any scan of said reference objects or said target object.

34. The method of claim 1, wherein each of said calibration objects avoid elements having a ratio of atomic weight to atomic number of greater than 2.1.

35. The method of claim 1, wherein each of said calibration objects are homogeneous at a level of resolution of said scan.

36. The method of claim 1, wherein each of said calibration objects are homogeneous at a level of resolution of 0.2 mm or less.

37. The method of claim 1, wherein the same calibration objects are used during the scanning of the reference objects and target object.

38. The method of claim 1, wherein the reference objects have a similar or same cross-section in size and shape to said target object.

39. The method of claim 1, wherein said reference objects are circular or semi-circular.

40. The method of claim 1, wherein steps i. and iii. can be performed in any order.

41. The method of claim 1, wherein said uncorrected density and/or effective atomic number is based upon an average per slice of said scan of the target object.

42. The method of claim 1, wherein the corrected bulk density is based upon an average per slice of said scan in view of said bulk density corrections.

43. The method of claim 1, wherein said uncorrected density and/or effective atomic number is based upon an average of entire scan of the target object.

44. The method of claim 1, wherein the corrected bulk density is based upon an average of entire scan in view of said bulk density corrections.

45. The method of claim 1, wherein obtaining a functional relationship between bulk density error and effective atomic number using scan values from the reference objects and the calibration objects comprises
   i. scanning the reference objects and calibration objects in a X-ray CT scanner, and
   ii. recording the high and low CT values from the X-ray CT scans, and
   iii. averaging the high and low CT values in each X-Y plane of the reference objects and calibration objects, and
   iv. using the known bulk density and effective atomic number of the calibration objects and their respective CT values to calculate a functional relationship between bulk density error and effective atomic number.

46. The method of claim 1, wherein the obtaining bulk density corrections using the functional relationship between bulk density error and effective atomic number from the reference objects, and the effective atomic number for the target object comprises an absolute bulk density correction and/or relative bulk density correction.

47. The method of claim 1, wherein the obtaining corrected bulk density using the bulk density corrections comprises applying absolute bulk density correction and/or relative bulk density correction.

48. A method for estimating the bulk density of a target object comprising:
   i. obtaining measurements of bulk density and effective atomic number from a set of objects including two or more reference objects with known bulk density;
   ii. expressing an error of the reference objects' bulk density obtained from the measurement in step i as a function of the effective atomic number of said reference objects;
   iii. obtaining measurements of bulk density and effective atomic number from the target object with unknown bulk density;
   iv. predict the error of the target object's bulk density obtained from the measurement in step iii using the effective atomic number of the target object obtained in step iii and bulk density error function obtained in step ii;
   v. adjusting the value of target object's bulk density obtained from the measurement in step iii by the value of the error predicted in step iv.

49. The method of claim 48, wherein said reference objects are rock samples, well core samples, or partial well core samples.

50. The method of claim 48, wherein the measurements of the bulk density and the atomic number from the reference objects in step i are performed by scanning the reference objects and interpreting the values produced by the scanning.

* * * * *